United States Patent [19]

Müller et al.

[11] 4,242,145

[45] Dec. 30, 1980

[54] PROCESS FOR THE SIMULTANEOUS PRODUCTION OF FRUCTOSE AND GLUCONIC ACID FROM GLUCOSE-FRUCTOSE MIXTURES

[75] Inventors: Hans-Rudolf Müller; Werner Kündig, both of Schaffhausen; Alfred Hedinger, Thayngen, all of Switzerland

[73] Assignee: Merck Patent Gesellschaft mit beschränkter Haftung, Darmstadt, Fed. Rep. of Germany

[21] Appl. No.: 13,634

[22] Filed: Feb. 21, 1979

[30] Foreign Application Priority Data

Feb. 20, 1978 [CH] Switzerland .......................... 1809/78

[51] Int. Cl.³ .......................... C13K 3/00; C13K 11/00; C07C 59/105
[52] U.S. Cl. .................................... 127/46 R; 127/41; 127/42; 536/1; 562/587
[58] Field of Search .................... 562/587; 127/30, 34, 127/42, 46 R; 536/1

[56] References Cited

U.S. PATENT DOCUMENTS

| | | | |
|---|---|---|---|
| 2,567,060 | 9/1951 | Docal | 127/53 |
| 2,949,389 | 8/1960 | Murtaugh | 127/36 |

FOREIGN PATENT DOCUMENTS 786288 11/1957 United Kingdom .

OTHER PUBLICATIONS

H. S. Isbell, "Methods in Carbohydrate Chem.", 101. II, R. L. Whistler, ed., 13–14, Academic Press, New York, 1963.
K. Heyns, Liebigs Ann. Chem., 558, 177–187 (1947).

*Primary Examiner*—Sidney Marantz
*Attorney, Agent, or Firm*—Millen & White

[57] ABSTRACT

A process for the simultaneous production of fructose and of gluconic acid from glucose-fructose mixtures and/or from invert sugar by the selective oxidation of the glucose proportion, wherein oxygen and/or air, activated by noble metal catalysts, are utilized as the oxidizing agents; the oxidation is conducted in a pH range of about 8 to 10; and the oxidation is terminated after the formation of 1 equivalent of carboxylic acid per mole of glucose employed.

The thus-obtained gluconic acid can subsequently be separated from the unchanged fructose in a simple way and practically quantitatively, and can be isolated as the salt.

7 Claims, No Drawings

PROCESS FOR THE SIMULTANEOUS PRODUCTION OF FRUCTOSE AND GLUCONIC ACID FROM GLUCOSE-FRUCTOSE MIXTURES

BACKGROUND OF THE INVENTION

The invention relates to a process for the simultaneous production of fructose and of gluconic acid from glucose-fructose mixtures and/or from invert sugar.

Although this problem has existed for a long time, it has not as yet been solved in a technically flawless way.

U.S. Pat. No. 2,567,060 and DOS [German Unexamined Laid-Open Application] 2,130,994 (published on Dec. 30, 1971) disclose subjecting a mixture of glucose (dextrose) and fructose to an electrochemical oxidation wherein glucose is oxidized to gluconic acid and separated as sparingly soluble calcium gluconate; fructose is isolated from the mother liquor. The fructose yield is relatively low, since a substantial proportion thereof is destroyed under the conditions of the electrochemical oxidation in a weakly alkaline medium.

In a similar fashion, attempts have been made to convert invert sugar into calcium gluconate and fructose by selective oxidation with bromine in the presence of calcium hydroxide. This process is expensive and cumbersome; it requires the regeneration of the bromine and, additionally, an essential portion of the fructose is also destroyed in this process.

It is known that fructose is very delicate. In strongly salt-containing solutions, fructose is already unstable, especially under heat; alkalis effect a very rapid destruction of fructose.

To preclude the destruction of fructose by the effect of the oxidizing agent, it has been suggested to subject glucose to a biochemical oxidation in a neutral to weakly acidic medium by the action of spores of *Aspergillus niger* [Murtaugh et al., U.S. Pat. No. 2,949,389; Sato et al., Chem. Abstr. 68:113323e (1968), and Kulhanek et al. Listy Cukrov 1972:88(2), 31–5 (Chem. Abstr. 77:21923h [1972])] or of *Aerobacter aerogenes* [Dalby et al., J. Microbiol. 1:733–42 (1955) (Chem. Abstr. 50:3517g [1956])].

However, this method is not optimally suited for technical production purposes. Too many by-products are encountered. The available microorganisms are furthermore inadequate in their efficiency. Also, a high dilution must be employed which considerably impedes the isolation of the readily water-soluble products.

Rao et al. (J. Electrochem. Soc. 1969:116[3], 334–7) describe the electrochemical oxidation of glucose to gluconic acid in a neutral medium. The thus-produced acid is, however, absorbed on the platinum-plated platinum electrode and prevents the continuance of electrolysis. This experiment showed that the electrochemical oxidation takes place satisfactorily only in an alkaline medium; according to experience, under all tested conditions, such a large proportion of the fructose is destroyed that this process cannot be considered from an economical viewpoint.

SUMMARY OF THE INVENTION

It is therefore an object of the present invention to provide a surprisingly simple, high-yield process which can be conducted on any desired scale, for the practically quantitative oxidation of glucose in glucose-fructose mixtures without any appreciable destruction of fructose, which process either lacks the aforedescribed disadvantages of the heretofore known methods or exhibits such disadvantages only to a greatly diminished degree.

It has been found that practically glucose-free fructose and gluconic acid and/or the salts thereof are obtained in high yields and practically free of by-products by the selective oxidation of the glucose proportion in glucose-fructose mixtures and/or of invert sugar, if the oxidizing agent employed is oxygen and/or air activated by noble metal catalysts and if the oxidation is conducted under conditions wherein the glucose is oxidized maximally completely to gluconic acid without the fructose being attacked during this process. According to the invention, these conditions are met if the oxidation is conducted at a pH of 8–10 and is immediately terminated when 1 equivalent of carboxylic acid per mole of glucose employed has been produced.

Accordingly, the invention relates to a process for the simultaneous production of fructose and of gluconic acid and/or the salts thereof from glucose-fructose mixtures and/or from invert sugar by the selective oxidation of the glucose proportion, characterized in that oxygen and/or air activated by a noble metal catalyst is utilized as the oxidizing agent; the oxidation is conducted in a pH range of about 8 to 10; and the oxidation is terminated after the formation of 1 equivalent of carboxylic acid and/or carboxylate ion per mole of glucose employed.

DETAILED DISCUSSION

The process of this invention is surprising, since it is known to oxidize fructose with air on a 5% platinum catalyst in an aqueous $NaHCO_3$ solution (indicated pH ranges between 5.8 and 8.7) to produce 2-keto-d-gluconic acid. Since it is known, on the other hand, that the stability maximum of fructose is at pH values of between 3.3 and 5, it was to be assumed that the fructose would be even more unstable in the alkaline range at higher pH values. However, in accordance with this invention, high yields are obtained precisely in the alkaline range.

Advantageously almost equimolar mixtures of glucose and/or fructose, e.g. the natural invert sugar, are utilized. However, it is also possible to employ mixtures containing excess fructose; thus, the glucose content of the mixtures usable according to the invention ranges suitably between about 10% and about 90%, and the fructose content is correspondingly between about 90% and about 10%.

Suitable noble metal catalysts include, in particular, commercially available palladium and platinum catalysts which can be used in finely divided form or on supports. Suitable supports are, for example, activated carbon, calcium carbonate, strontium carbonate, or kieselguhr. Preferred is 2–10% palladium carbon. The amount of the catalyst (without the support) ranges preferably between 0.1 and 1% by weight, especially between 0.1 and 0.5% by weight, based on the amount of glucose and fructose. Most suitable as oxidizing agents proved to be oxygen-nitrogen mixtures with an oxygen proportion of about 10 to >50%, e.g. air, wherein the reaction velocity is approximately proportional to the oxygen proportion. A higher oxygen proportion is possible, but is normally expensive from a technical viewpoint and thus unfavorable due to the expenses involved. With a lower oxygen proportion, the oxidation proceeds more slowly than is technically desirable. The process can be conducted under excess pressure (up to about 200 atmospheres), under normal pressure, or under subatmospheric pressure. Advantageously, normal pressure or slightly excess pressure is utilized (from about 0.01 to 0.1 bar).

The process is suitably carried out in an aqueous, preferably concentrated (about 10% to >50%) aqueous solution, wherein the thus-formed gluconic acid is constantly neutralized, e.g., by the addition of alkali metal or alkaline earth metal hydroxides, especially aqueous sodium hydroxide solution, so that a pH of above 7, preferably between 8 and 10, especially between 9 and 10, is being maintained.

The selective oxidation is advantageously conducted at a temperature of 10°–50°, preferably at 20°–35°. It has been found that the reaction proceeds only insubstantially more slowly at 25° than at 35°–40°, but that colorless solutions are produced at the lower temperature while solutions of a slightly yellow color are formed during the oxidation at 35°–45°.

The reaction must be terminated after consumption of the stoichiometric amount of oxygen or the formation of 1 equivalent of carboxylic acid and/or carboxylate ion per mole of glucose employed, since otherwise the thus-formed gluconic acid as well as the fructose are further oxidized, producing several acidic compounds. Consequently, brief reaction times are necessary for a selective conductance of the process. Normally, the oxidation of glucose to gluconic acid is finished after about 1–14 hours, in case of an optimum control of the process, after about 1.5–3 hours.

The instant at which the reaction must be terminated can readily be determined from the consumption of base required for the constant neutralization of the thus-formed carboxylic acid.

In particular, the invention relates to a process for the simultaneous production of fructose and of gluconic acid and/or the salts thereof from glucose-fructose mixtures and/or from invert sugar by the selective oxidation of the glucose proportion, characterized in that an aqueous solution of the mixture is treated with air in the presence of a palladium catalyst at 25°–40° and at a pH value of 9–10.

The yield of gluconate in the present process according to this invention ranges from 93 to 95% of theory, wherein the gluconate has a concentration of 98–101%. The yield of fructose in the mother liquor is 90–95% of theory.

The product can be worked up in various ways. Thus, it is possible upon termination of the reaction, after the catalyst has been removed and the filtrate has been concentrated to about one-half its volume, to separate the gluconic acid in the form of its crystallized sodium salt practically quantitatively by adding about 1–5 parts by volume of methanol; with this mode of operation, the originally present fructose is recovered in the mother liquor to an extent of more than 90%.

The separation of fructose and gluconic acid by treating a highly concentrated aqueous solution containing gluconate and fructose by the addition of ethanol has been conventional. However, in this process two highly viscous liquid phases are obtained, wherein a clear separation and working up of the products is very difficult. In contrast thereto, with the use of methanol to separate the gluconic acid and/or the gluconate, a crystalline, pure product is obtained.

If it is intended to produce calcium gluconate in place of sodium gluconate, it is possible to employ calcium hydroxide instead of sodium hydroxide during the oxidation reaction for the constant neutralization of thus-formed acid; or the thus-obtained sodium gluconate can be converted into calcium gluconate in accordance with known methods.

All temperatures herein are indicated in degrees Celsius.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

99.1 g. of glucose monohydrate (0.5 mole) and 90.1 g. of fructose (0.5 mole) are dissolved in water; water is added to a volume of 850 ml.; and then the mixture is combined with 10 g. of 5% palladium carbon catalyst and subjected to an oxidation with 21% oxygen. The pH of the reaction solution is maintained between 9.2 and 9.5 by the addition of sodium hydroxide solution. The oxygen-nitrogen mixture is finely distributed in the reaction solution. The oxygen content of the gaseous stream is measured at the inlet and at the outlet and adjusted to the desired value by way of control valves by adding oxygen or nitrogen. The reaction temperature is maintained at 35°.

| | Course of Reaction | | | Addition of NaOH |
|---|---|---|---|---|
| | | Oxygen Content | | |
| Time min. | pH | Inlet % | Outlet % | 39 g./100 ml. ml. |
| 0 | | 10 | 6 | 0 |
| 20 | 9.5 | 15 | 12 | 4.1 |
| 35 | 9.2 | 18 | 14 | 7.7 |
| 50 | 9.2 | 21 | 16 | 13.7 |
| 65 | 9.2 | 21 | 16 | 20.2 |
| 80 | 9.2 | 21 | 16.3 | 26.9 |
| 95 | 9.2 | 21 | 16 | 33.1 |
| 110 | 9.3 | 21 | 14 | 38.0 |
| 125 | 9.3 | 21 | 14.5 | 41.9 |
| 140 | 9.2 | 21 | 17 | 47.1 |
| 154 | 9.4 | 21 | 17.5 | 51.4 |

The mother liquor freed of the catalyst by filtration contains 97% of the stoichiometric quantity of fructose and 96% of sodium gluconate (determined by gas chromatography). The mother liquor is concentrated to one-half its volume at 35°. Under agitation 900 ml. of methanol is added to the mixture. After allowing the mixture to stand overnight, the thus-formed sodium gluconate is filtered off, washed with a small amount of methanol, and dried. Yield: 125 g. (91% of theory); concentration 99% of theory.

The fructose-containing mother liquor is concentrated to about 300 ml. According to determination by gas chromatography, the mother liquor contains 83.8 g. of fructose (93% of theory). The fructose solution can be utilized as such, reduced to a mixture of mannitol and sorbitol, or crystallized in accordance with conventional methods.

EXAMPLE 2

The same results as in Example 1, lying within experimental scattered values, are obtained by replacing the glucose monohydrate and the fructose by invert sugar syrup made of 342 g. of cane sugar and 513 ml. of water with a degree of inversion of 99.5%, and employing 350 ml. of water for replenishing the volume instead of 850 ml. of water.

EXAMPLE 3

Syrups obtained by the isomerization of, respectively, 1 mole of glucose and having a proportion of 85–52% glucose and 15–48% fructose are selectively oxidized as set forth in Example 1.

The thus-formed sodium gluconate is separated and obtained as a crystallized product in yields of 87–94% of theory. The mother liquors contain 87–94% of the theoretically possible quantity of fructose (determined by gas chromatography).

EXAMPLE 4

Variation of the Reaction Conditions.

Mode of operation and apparatus as described in Example 1. Batch size respectively 0.5 mole of glucose and of fructose; consumption of NaOH to neutralize the thus-formed acid is 99.3–100.4% of theory (=0.5 mole).

Variation of the amount of catalyst and the type of catalyst, pH, temperature and oxygen content of the reaction gas (oxygen-nitrogen mixture).

4.1 Variation of the amount of catalyst (5% palladium carbon); reaction temperature 35°; pH 9.3–9.8; oxygen content 21%.

| Amount of Catalyst g. | Reaction Time min. | Yield % of Theory | |
|---|---|---|---|
| | | Na Gluconate | Fructose |
| 2.5 | 415 | 89 | 90 |
| 2.5 | 345 | 93.4 | 90 |
| 5 | 182 | 89 | 94 |
| 5 | 197 | 86 | 94 |
| 7.5 | 138 | 94 | 96 |
| 7.5 | 174 | 95 | 95 |
| 10 | 129 | 94 | 96 |
| 10 | 153 | 94 | 94 |

4.2 Variation of the palladium content (1, 5 and 10% Pd carbon). Catalyst quantity 10 g; reaction temperature 35°; pH 9.3–9.8; oxygen content 21%.

| Palladium Content of Pd Carbon in % | Reaction Time min. | Yield % of Theory Fructose |
|---|---|---|
| 1 | >780 | 78 |
| 1 | >780 | 79 |
| 5 | 106 | 91 |
| 5 | 183 | 91 |
| 10 | 132 | 90 |

4.3 Variation of the pH. Catalyst 10 g. of 5% Pd/C; reaction temperature 35°; oxygen content 21%.

| pH Range | Reaction Time min. | Yield % of Theory | |
|---|---|---|---|
| | | Na Gluconate | Fructose |
| 7.5–8.8 | 195 | 76 | 88 |
| 7.8–8.9 | 255 | 74 | 91 |
| 8.3–9.3 | 140 | 80 | 91 |
| 8.2–9.5 | 136 | 80 | 91 |
| 9.0–9.5 | 130 | 96 | 95 |
| 9.3–9.6 | 130 | 96 | 97 |
| 9.0–9.8 | 122 | 94 | 98 |

4.4 Variation of the reaction temperature. Catalyst 10 g. 5% Pd/C; pH 9.3–9.8; oxygen content 21%.

| Reaction Temp °C. | Reaction Time min. | Yield % of Theory | | Remarks |
|---|---|---|---|---|
| | | Na Gluconate | Fructose | |
| 20–35 | 537 | 80 | 80 | rising |
| 35–20 | 152 | 93 | 98 | dropping |
| 35–20 | 158 | — | — | dropping |
| 35 | 122 | 91 | 91 | (1) |
| 35 | 117 | 92 | 92 | (1) |
| 40 | 90 | — | — | (1) |

(1) Reaction solution somewhat yellowish 4.5 Variation of the oxygen content in the oxygen-nitrogen mixture. Catalyst 10 g. 5% Pd/C; temperature 35°; pH 9.3–9.8.

| Oxygen Content in % | Reaction Time min. |
|---|---|
| 10 | 330 |
| 15 | 220 |
| 21 | 140 |
| 30 | 100 |

The shorter the reaction time, the higher the yields and the quality of the thus-obtained products.

EXAMPLE 5

Repeated Use of Catalyst.

The catalyst—10 g. 5% palladium carbon—utilized for a standard batch according to Example 1 can be repeatedly utilized without a measurable decrease in activity.

The filtered-off catalyst from the preceding batch is added to the aqueous glucose-fructose solution of the subsequent batch. The thus-obtained reaction solution is treated as set forth in Example 1.

| Number of Subsequent Batches with the Same Catalyst | Reaction Time min. | Yield % of Theory | |
|---|---|---|---|
| | | Na Gluconate | Fructose |
| 1 | 137 | 93 | 98 |
| 2 | 132 | 93 | 97 |
| 5 | 126 | 96 | 97 |
| 10 | 128 | 98 | 94 |
| 15 | 139 | 98 | 95 |
| 20 | 169 | 96 | 93 |
| 25 | 146 | 96 | 98 |

The undiminishedly short reaction time and the yields demonstrate the unreduced efficiency of the catalyst.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the simultaneous production of fructose, a salt thereof or a mixture thereof, and of gluconic acid, a salt thereof or a mixture thereof, from a glucose-fructose mixture, by selectively oxidizing the glucose, the improvement which comprises selectively oxidizing the glucose, at a pH of about 8-10, with oxygen, activated by a noble metal catalyst; and terminating the oxidizing step upon the formation of 1 equivalent, per mole of glucose employed, of the total amount of carboxylic acid and carboxylate ion produced during the oxidizing step.

2. The process of claim 1, wherein the glucose-fructose mixture is invert sugar.

3. The process of claim 1, which comprises selectively oxidizing the glucose with oxygen, air or a mixture thereof.

4. The process of claim 1, wherein the temperature is 10°-50° C. during the oxidation.

5. The process of claim 1, which comprises selectively oxidizing glucose in an aqueous solution of a mixture of glucose and fructose with air in the presence of a palladium catalyst at 25°-40° C. and at a pH of 9-10.

6. The process of claim 1, which further comprises separating the formed gluconic acid in the form of its sodium salt from the fructose by extracting with methanol.

7. In a process for the simultaneous production of fructose, a salt thereof or a mixture thereof, and of gluconic acid, a salt thereof or a mixture thereof, from a glucose-fructose mixture, by selectively oxidizing the glucose, the improvement which comprises selectively oxidizing the glucose, at a pH of above 7, with oxygen, activated by a noble metal catalyst; and terminating the oxidizing step upon the formation of 1 equivalent, per mole of glucose employed, of the total amount of carboxylic acid and carboxylate ion produced during the oxidizing step or upon consumption of the stoichiometric amount of oxygen.

* * * * *